US006899848B1

(12) United States Patent
Chen et al.

(10) Patent No.: US 6,899,848 B1
(45) Date of Patent: May 31, 2005

(54) AUTOMATED SAMPLE TREATMENT SYSTEM: APPARATUS AND METHOD

(75) Inventors: Chih-Chung Chen, Reno, NV (US); Gregory Gulla, Reno, NV (US); Sean Patrick Kelley, Sparks, NV (US)

(73) Assignee: Hamilton Company, Reno, NV (US)

( * ) Notice: Subject to any disclaimer, the term of this patent is extended or adjusted under 35 U.S.C. 154(b) by 442 days.

(21) Appl. No.: 09/795,853

(22) Filed: Feb. 27, 2001

(51) Int. Cl.[7] .................. G01N 21/00; G01N 31/00; B32B 27/04; B01L 3/02; B01L 3/11
(52) U.S. Cl. .................. 422/63; 422/65; 422/66; 422/68.1; 422/100; 422/101
(58) Field of Search .................. 422/63–67, 68.1, 422/100, 99, 101

(56) References Cited

U.S. PATENT DOCUMENTS

| | | |
|---|---|---|
| 4,113,434 A | 9/1978 | Tanaka et al. |
| 4,184,961 A | 1/1980 | Rynde et al. |
| 4,766,082 A | 8/1988 | D'Autry |
| 4,771,642 A | 9/1988 | Parth et al. |
| 4,810,471 A | 3/1989 | Wachob et al. |
| 4,846,970 A | 7/1989 | Bertelsen et al. |
| 4,869,116 A | 9/1989 | Meyrat et al. |
| 4,895,706 A | 1/1990 | Root et al. |
| 4,927,604 A | 5/1990 | Mathus et al. |
| 4,948,564 A | 8/1990 | Root et al. |
| 4,952,518 A | 8/1990 | Johnson et al. |
| 4,976,926 A | 12/1990 | Matkovich |
| 5,141,719 A | 8/1992 | Fernwood et al. |
| 5,190,666 A | 3/1993 | Bisconte |
| 5,217,619 A | 6/1993 | Redmond, Jr. et al. |
| 5,219,528 A | 6/1993 | Clark |
| 5,227,137 A | 7/1993 | Monti et al. |
| 5,232,665 A * | 8/1993 | Burkovich et al. ........... 422/65 |
| 5,232,666 A | 8/1993 | Longman et al. |
| 5,260,028 A | 11/1993 | Astle |
| 5,273,718 A | 12/1993 | Skold et al. |
| 5,283,039 A | 2/1994 | Aysta |
| 5,372,037 A | 12/1994 | Butt |
| 5,380,437 A | 1/1995 | Bertoncini |
| 5,401,637 A | 3/1995 | Pocock |
| 5,415,051 A | 5/1995 | Rokugawa et al. |

(Continued)

OTHER PUBLICATIONS

Applied Biosystems, "6700 Automated Nucleic Acid Workstation" Nov. 2000—Entire Brocure.

*Primary Examiner*—Jill Warden
*Assistant Examiner*—Brian R. Gordon
(74) *Attorney, Agent, or Firm*—Bernhard Kreten (57) ABSTRACT

A sample treatment system for automated extraction of compounds is disclosed. The system includes a housing defining an enclosure including a top cover having open ended chambers to receive sample plates on an interposed carriage frame, an automated shuttle means for lateral transportation and vertical lifting of the carriage frame to selectively address the chamber below the sample plate for the throughpassage of fluid from the sample plate and urged by a vacuum pump for evacuating air from a chamber to a degree below atmospheric pressure for through passage of fluid from the sample plate to either a waste plate or a collection plate. The shuttle means includes motor drives for precisely laterally and vertically positioning the carriage frame.

6 Claims, 8 Drawing Sheets

U.S. PATENT DOCUMENTS

| | | | | |
|---|---|---|---|---|
| 5,424,038 A | | 6/1995 | Benz et al. | |
| 5,490,971 A | | 2/1996 | Gifford et al. | |
| 5,529,694 A | | 6/1996 | Strickler | |
| 5,620,894 A | | 4/1997 | Berger et al. | |
| 5,624,815 A | | 4/1997 | Grant et al. | |
| 5,645,723 A | | 7/1997 | Fujishiro et al. | |
| 5,660,792 A | | 8/1997 | Koike | |
| 5,770,157 A | | 6/1998 | Cargill et al. | |
| 5,876,670 A | * | 3/1999 | Mitsumaki et al. | 422/65 |
| 5,888,830 A | | 3/1999 | Mohan et al. | |
| 5,928,952 A | * | 7/1999 | Hutchins et al. | 436/50 |
| 5,955,373 A | * | 9/1999 | Hutchins et al. | 436/48 |
| 5,972,295 A | * | 10/1999 | Hanawa et al. | 422/65 |
| 6,068,393 A | * | 5/2000 | Hutchins et al. | 700/112 |
| 6,117,392 A | * | 9/2000 | Hanawa et al. | 422/65 |
| 6,133,045 A | * | 10/2000 | Johnson et al. | 436/177 |
| 6,159,368 A | * | 12/2000 | Moring et al. | 210/321.75 |
| 6,267,927 B1 | * | 7/2001 | Pomar Longedo et al. | 422/65 |
| 6,309,608 B1 | * | 10/2001 | Zhou et al. | 422/131 |
| 6,444,171 B1 | * | 9/2002 | Sakazume et al. | 422/65 |
| 6,491,873 B2 | * | 12/2002 | Roberts et al. | 422/101 |
| 6,521,183 B1 | * | 2/2003 | Burri et al. | 422/65 |
| 6,592,826 B1 | * | 7/2003 | Bloecker et al. | 422/101 |
| 6,599,749 B1 | * | 7/2003 | Kodama et al. | 436/47 |
| 6,649,128 B1 | * | 11/2003 | Meyer et al. | 422/63 |
| 2002/0150505 A1 | * | 10/2002 | Reed et al. | 422/63 |
| 2002/0176803 A1 | * | 11/2002 | Hamel et al. | 422/100 |

* cited by examiner

AUTOMATED SAMPLE TREATMENT SYSTEM: APPARATUS AND METHOD

FIELD OF THE INVENTION

The instant invention relates generally to a robotic sample treatment system and, in particular, to a variably controllable vacuum extraction system including a vacuum manifold with both waste and collection sites communicating with a vacuum pump.

BACKGROUND OF THE INVENTION

Sample preparations in medical diagnostics, the pharmaceutical industries, chemical industries as well as people doing DNA work require many precise liquid handling steps, such as: transfer of samples, dilutions, additions of reagents, transfer of reaction mixtures, etc. Automated liquid handling systems have been developed and are commercially available in the form of programmable pipetting work stations. These automated systems reduce the manual labor involved in the liquid handling and processing of samples. See for example, U.S. Pat. No. 6,033,911, owned by applicant.

However, these systems are not completely automatic and still require manual manipulation and user intervention, especially when using a manual vacuum manifold system with the pipetting work station. The processing of liquids still requires human intervention and manual manipulation. Typically, the user is required to place a filter plate on top of the manual vacuum box and then the filter plate is filled with a plurality of samples. Once the filter plate is filled with samples, the user has to manually manipulate the vacuum during the wash steps of the extraction process. Once the wash step of the extraction process is completed, the user carefully removes the filter plate containing the remaining constituents which are being collected. The user then places a collection plate into the vacuum box and then places the filter plate on top of the collection plate and then manually manipulates the vacuum to extract the constituent of interest. Thus, the user is constantly interacting with the system during the collection of samples.

Thus, existing systems have short comings that limit their efficiency. For example, some analytical laboratories process hundreds of samples using solid phase extraction or other techniques. Since the steps are highly repetitive, automated systems are needed to reduce the manual labor involved in the liquid handling and processing steps. In addition, user intervention and manual operations reduce the efficiency of an otherwise automated analytical system.

Therefore, there is a need for an apparatus and method for performing analytical procedures without the need for operator intervention and minimizing the manual tasks before, during and after the analytical procedures.

In addition, there is a need for an apparatus and method which provides automated vacuum control to enhance flow rates through the sorbing media or frit, thus providing good recoveries and throughput of flow rate dependent compounds. In addition, a system having an automated variable vacuum control would mitigate well to well cross talk tendencies.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
| --- | --- | --- |
| 4,113,434 | Sep. 12, 1978 | Tanaka, et al. |
| 4,184,961 | Jan. 22, 1980 | Rynde, et al. |
| 4,771,642 | Sep. 20, 1988 | Parth, et al. |
| 4,766,082 | Aug. 23, 1988 | Marteau D'Autry |
| 4,810,471 | Mar. 7, 1989 | Wachob, et al. |
| 4,846,970 | Jul. 11, 1989 | Bertelsen, et al. |
| 4,869,116 | Sep. 26, 1989 | Meyrat, et al. |
| 4,895,706 | Jan. 23, 1990 | Root, et al. |
| 4,927,604 | May 22, 1990 | Mathus, et al. |
| 4,948,564 | Aug. 14, 1990 | Root, et al. |
| 4,952,518 | Aug. 28, 1990 | Johnson, et al. |
| 4,976,926 | Dec. 11, 1990 | Matkovich |
| 5,141,719 | Aug. 25, 1992 | Fernwood, et al. |
| 5,190,666 | Mar. 2, 1993 | Bisconte |
| 5,217,619 | Jun. 8, 1993 | Redmond, Jr., et al. |
| 5,219,528 | Jun. 15, 1993 | Clark |
| 5,227,137 | Jul. 13, 1993 | Monti, et al. |
| 5,232,666 | Aug. 3, 1993 | Longman, et al. |
| 5,260,028 | Nov. 9, 1993 | Astle |
| 5,273,718 | Dec. 28, 1993 | Sköld, et al. |
| 5,283,039 | Feb. 1, 1994 | Aysta |
| 5,372,037 | Dec. 13, 1994 | Butt |
| 5,380,437 | Jan. 10, 1995 | Bertoncini |
| 5,401,637 | Mar. 28, 1995 | Pocock |
| 5,415,051 | May 16, 1995 | Rokugawa, et al. |
| 5,424,038 | Jun. 13, 1995 | Benz, et al. |
| 5,490,971 | Feb. 13, 1996 | Gifford, et al. |
| 5,529,694 | Jun. 25, 1996 | Strickler |
| 5,620,894 | Apr. 15, 1997 | Barger, et al. |
| 5,624,815 | Apr. 29, 1997 | Grant, et al. |
| 5,645,723 | Jul. 8, 1997 | Fujishiro, et al. |
| 5,660,792 | Aug. 26, 1997 | Koike |
| 5,770,157 | Jun. 23, 1998 | Cargill, et al. |
| 5,888,830 | Mar. 30, 1999 | Mohan, et al. |

OTHER PRIOR ART—NON PATENT LITERATURE DOCUMENTS

Applied Biosystems, "6700 Automated Nucleic Acid Workstation", November 2000, entire brochure.

D'Autry discloses a moveable carriage (120) which enables a waste receptacle or individual tubes to be placed beneath an orifice of a cartridge.

SUMMARY OF THE INVENTION

U.S. Pat. No. 6,133,045, also owned by applicant, resolved many of these problems. However, the present invention takes this technology to a new level.

The instant invention provides an automated sample treatment system for automated extraction of genomic and plasmid DNA or simultaneous solid phase extraction of compounds. The sample treatment system is integrated with an automated pipetting work station and a robotic arm which automatically transfers treatment plates into and out of the system. The system includes an automated shuttle means for lateral transportation and vertical lifting of treatment plates over stationary waste and collection sites.

In a preferred form, the sample treatment system of the instant invention is integrated with the liquid handling capabilities of a programmable pipetting work station. The sample treatment system includes a vacuum manifold apparatus having a shuttle mechanism, a vacuum control apparatus and an electronic control system.

A robotic arm delivers sample treatment plates with respect to the vacuum manifold extraction system for further automation. A vacuum box has two distinct chambers defining two areas to individually receive vacuum: an elution area and a waste area. Each area has a vacuum port.

The vacuum control apparatus includes a vacuum pump which is operatively coupled to the vacuum areas via vacuum lines extending from the vacuum pump to each port of the vacuum box. Thus, when the vacuum pump is turned on, the vacuum area of one chamber is depressurized and the vacuum power will pull the liquid from a sample treatment plate during at least two processes detailed below. A liquid waste bottle is coupled to a drain in the vacuum box and a waste pump removes and stores waste liquid in the waste bottle.

A transport carriage is operatively coupled to a lift and transport mechanism all of which are disposed exteriorly of both chambers. Thus, the lift and transport mechanism is not exposed to the chemicals used in the system's chambers. The lift and transport mechanism moves to and from the elution chamber and waste chamber and is preferably dimensioned to cover only one chamber. This allows outside access to the exposed treatment plate (for example by pipetting station or robotic arm). As a consequence, when the chamber receiving the transport carriage is being "processed" (e.g., receiving vacuum) the other chamber is available for further external processing (e.g., removal/insertion via robotic arm, waste removal or pipetting). By sequestering the vacuum box into discrete, separate vacuum areas, the vacuum chamber volume is smaller and therefore requires a smaller vacuum pump.

Whereas U.S. Pat. No. 6,133,045 teaches pulling a vacuum through the waste bottle, the present invention utilizes a separate waste circuit, powered by its own pump. By having the vacuum pump on its own circuit, vacuum pump requirements are further lessened. Adjusting the vacuum pressure is also easier since the waste circuit is no longer an element.

OBJECTS OF THE INVENTION

Accordingly, a primary object of the instant invention is to provide a new, novel and useful sample treatment system: apparatus and method.

A further object of the instant invention is to provide a sample treatment system as characterized above which includes a vacuum manifold apparatus with both waste and collection sites.

Another further object of the instant invention is to provide a sample treatment system as characterized above which includes an automated vacuum based extraction apparatus.

Another further object of the instant invention is to provide a sample treatment system as characterized above which includes a computer interface system including a communication interface and in system programmability.

Another further object of the instant invention is to provide a sample treatment system as characterized above which is a stand alone functional module.

Viewed from the first vantage point, it is an object of the present invention to provide a sample treatment device, comprising in combination: a housing having plural chambers; a sample plate; means to expose said sample plate to one chamber in said housing; extraction means operating on the sample plate addressing the sample plate to the one chamber and in fluid communication, and shuttle means to selectively present the sample plate to one of the plural chambers for the throughpassage of fluid from the sample plate.

Viewed from the second vantage point, it is an object of the present invention to provide a method for treating a sample, the steps including: providing a housing with plural chambers; nesting a sample plate to address one of the chambers wherein the sample plate is in open fluid communication with both an interior area of the one chamber and exteriorly; evacuating air from the one chamber to a degree below atmospheric pressure for throughpassage of a fluid from the sample plate to the chamber; shuttling the sample plate to selectively address another chamber.

Viewed from the third vantage point, it is an object of the present invention to provide a sample treatment device, comprising in combination: a housing having plural chambers including means for receiving a sample plate in open fluid communication with both an interior of one said chamber and exteriorly; means for moving the sample plate to said plural chambers; and means for evacuating air from any of the plural chambers to a degree below atmospheric pressure for throughpassage of a fluid from the sample plate to the chamber presented with the sample plate.

Viewed from the fourth vantage point, it is an object of the present invention to provide a sample treatment device, comprising, in combination: housing having plural chambers, each including means for receiving a sample plate in open fluid communication both with an interior of one said chamber and exteriorly; said plural chambers including a waste chamber and a collection chamber; means for shuttling said sample plate to either said waste chamber or said collection chamber; and means for evacuating air from said chamber to a degree below atmospheric pressure to pull a fluid from the sample plate to either said waste or collection chamber when said sample plate is adjacent thereto.

Viewed from the fifth vantage point, it is an object of the present invention to provide a device to move fluid from a sample plate having plural samples oriented in open bottomed vertical tubes to a collection plate having a complemental number of open topped vertical tubes as the sample plate, comprising, in combination: a chamber to support the collection plate substantially horizontally; said sample plate supported on means to move said sample plate vertically to said chamber and adjacent said collection plate; a vacuum means in said chamber to draw fluid from said tubes in the sample plate; said vacuum means drawing samples from a bottom of said sample plate into said collection plate such that each sample in said sample plate is directed to a corresponding said vertical tube in said collection plate without cross-talk between adjacent tubes once said sample has been moved vertically proximate to said collection plate.

Viewed from the sixth vantage point, it is an object of the present invention to provide a method for treating samples, the steps including: placing a sample treatment plate on a sample support; robotically addressing the sample treatment plate with a pipetting mechanism; eluting and washing preparations contained in said sample treatment plate including applying a vacuum; and robotically removing the sample treatment plate.

Viewed from the seventh vantage point, it is an object of the present invention to provide a sample treatment workstation, comprising, in combination: a robotic pipetting means; a sample support for receiving a sample treatment plate and addressing said pipetting means; said sample support including eluting and washing means and a robotic arm having means to transfer sample treatment plates to and from said sample support.

These and other objects will be made manifest when considering the following detailed specification when taken in conjunction with the appended drawing figures.

DESCRIPTION OF PREFERRED EMBODIMENTS

Referring to the drawings, wherein like reference numerals denote like parts, numeral 300 (FIG. 2) is directed to the sample treatment workstation according to the present invention. In its essence, the workstation 300 includes a pipette station 100, a robotic arm 200 and a vacuum box 10.

Figure 1:
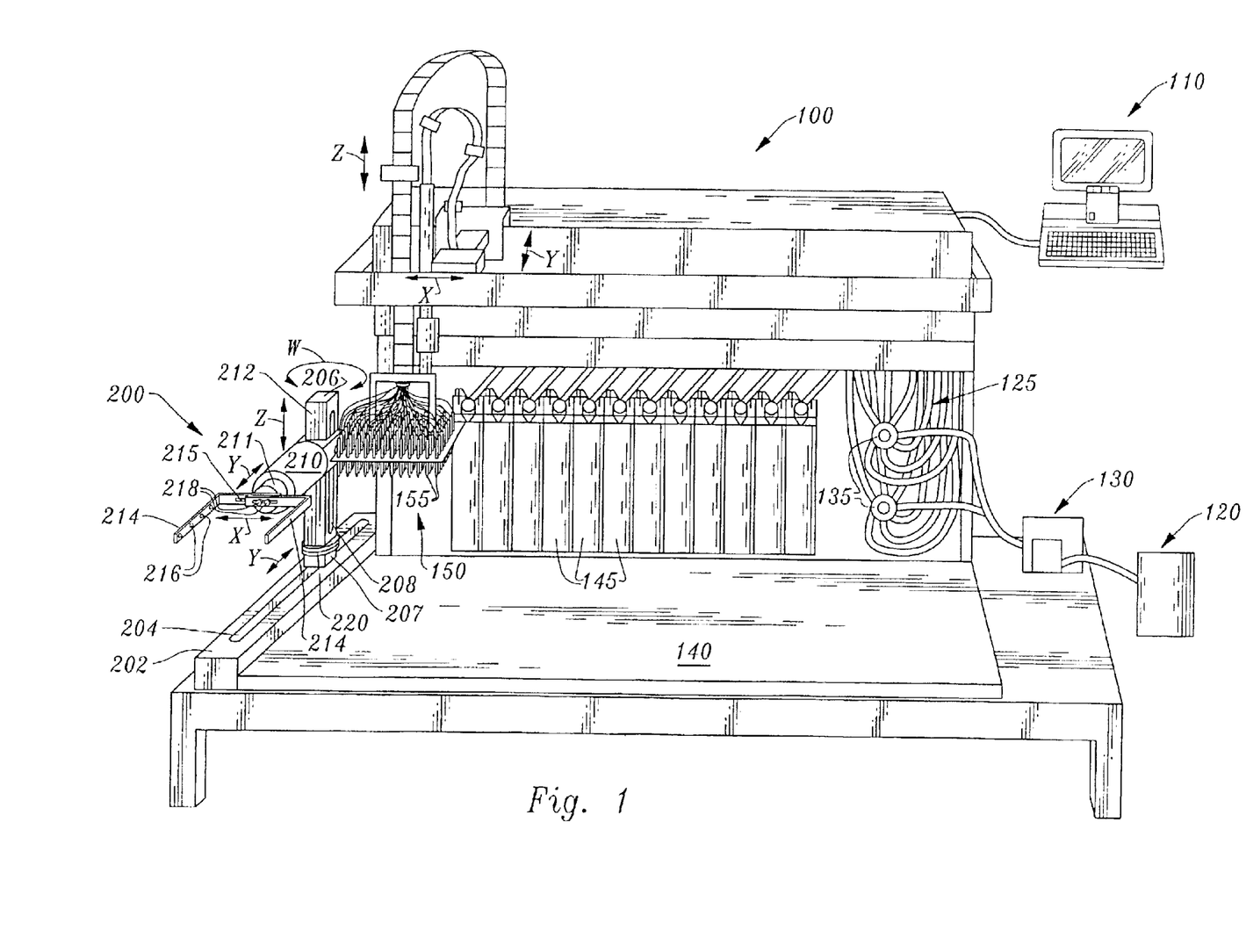
FIG. 1 is a from elevational view of the robotic sample processor and the robotic arm.

The pipette station 100 includes a work table 140 (FIG. 1) upon which the vacuum box 10 is placed. In addition, the pipette station 100 includes a probe assembly 150 which has three degrees of freedom as shown in FIG. 1 to include latitudinal translation along the direction of the arrow "X", longitudinal translation along the arrow "Y" and vertical translation along the arrow "Z" so that the probe assembly 150 can move along the length and width of the table and up and down. A source of fluid 120 is operatively coupled to a pump 130 which delivers the fluid to the probe assembly 150 by means of a fluidic network comprised of a series of tubes 125, valves 135 and discreet delivery units 145. The probe assembly 150 includes a multiplicity of individual probe tips 155 each of which can carry same or different fluids as dictated by the valves 135 and discrete delivery units 145 for urging fluid through the probe assembly 150. The probe assembly 150 is shown as having 96 tips 155 oriented in an 8×12 array. Other probe arrays and tip populations are possible. Control for the various fluids that pass through the probe assembly is controlled by a computer 110 which can also control the robotic arm 200 and vacuum box 10 and its sequencing protocols.

Figure 2:
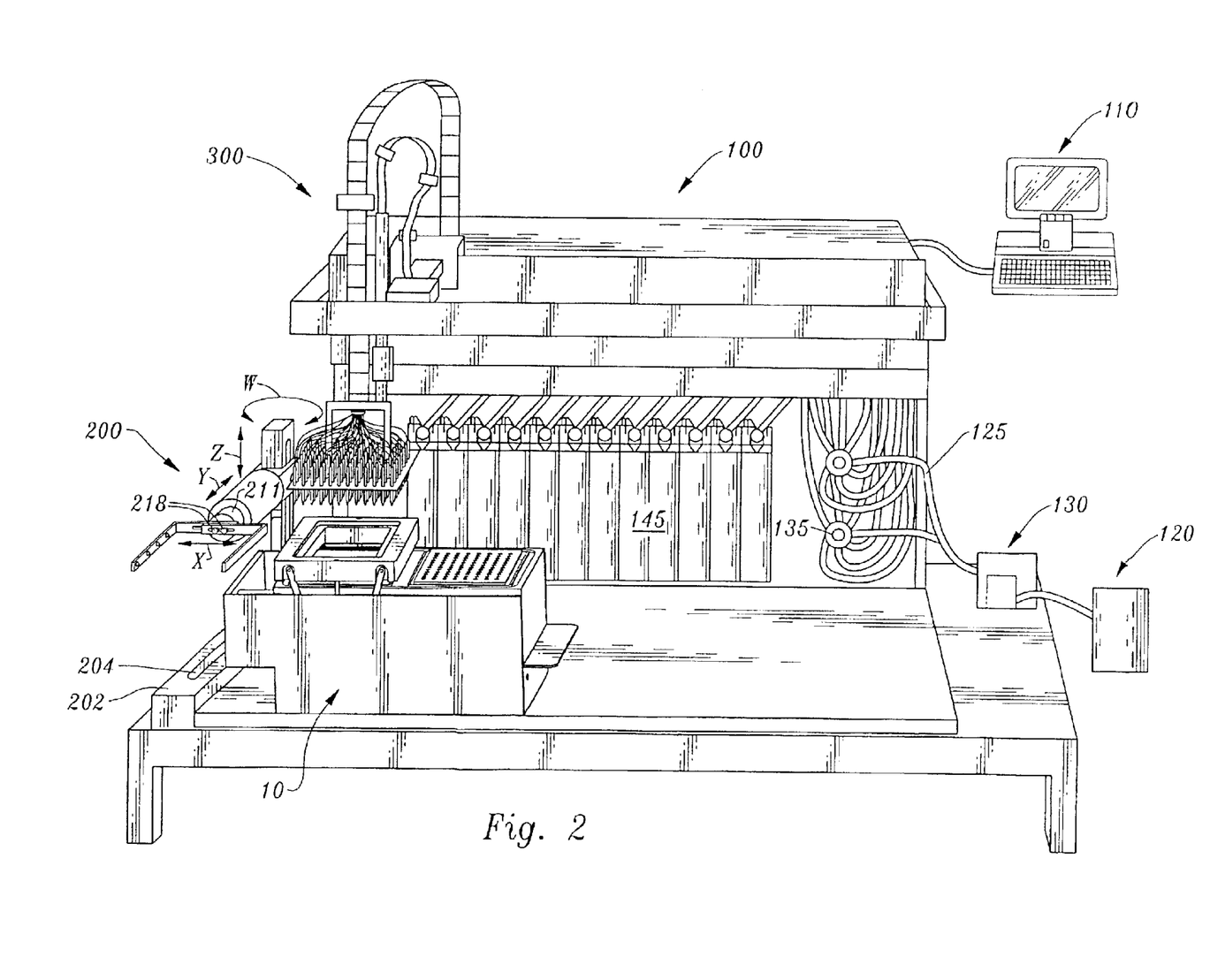
FIG. 2 is a front elevational view of the vacuum manifold apparatus shown disposed on the robotic sample processor adjacent the robotic arm.
Figure 4:
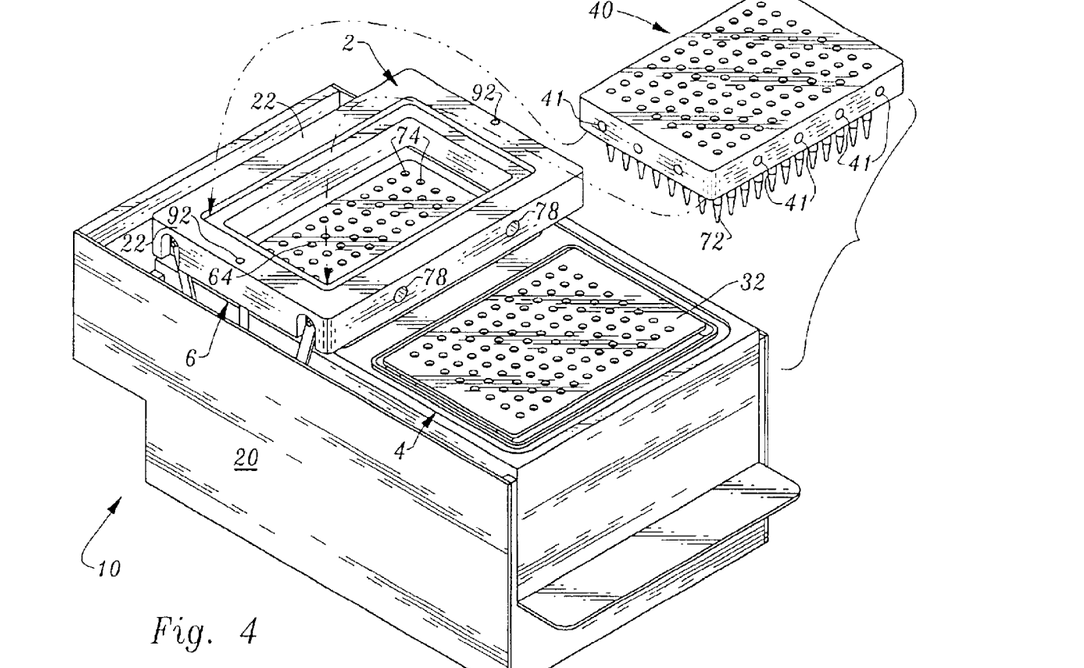
FIG. 4 is an upper perspective view of the vacuum manifold apparatus.

The robotic arm 200 includes a base 202 having a slot 204 extending along its length upon which a mast 206 is vertically disposed and adapted to slide within the slot 204 along the Y direction shown in FIGS. 1 and 2. In addition, the mast 206 is adapted to rotate about the double ended arrow "W" by virtue of its coupling to a stem 207 of the mast 206 via a swivel 220. The mast 206 includes a vertical slot 208 to allow vertical translation of a transversely oriented arm 210 along the direction of the double ended arrow "Z". The arm 210 is capable of telescopic extension along the direction of the double ended arrow "Y" by means of a telescopic rod 211 extensible within the arm 210. A free end of the telescopic rod 211 attaches to engaging fingers 214. The engaging fingers 214 are formed as two substantially L-shaped brackets which face each other to form a substantially "U" shaped structure. Each bracket has a leg proximate the rod 211 fitted with a slot 215. The slots 215 are in overlapping registry and held by pins 218 (one pin per leg fixed, the other pin slideably disposed in the other's slot 215) which inwardly allow the two opposed free ends of the L-shaped fingers to move along the double ended arrow "X". Thus, the spacing between the two pairs of L-shaped fingers 214 can be manipulated to grasp side edges of a sample plate 40 to be described. In order to assist in the engagement, each of the engaging fingers 214 includes retention pins 216 on their facing sides to nest within corresponding recesses 41 (FIG. 4) on the sample plate 40.

The sample plate 40 is dimensioned to lie atop vacuum box 10. Specifically, a carriage frame 2 (FIG. 4) is interposed between the sample plate 40 and a housing 20 of the vacuum box 10. The carriage frame 2 defines one component of a lift and transport carriage assembly which moves between a first and second position. In a first position, the carriage frame addresses a first (waste) chamber 4 formed within the housing 20. In a second position, the carriage frame addresses a second (elution) chamber 6 also formed in the housing 20.

Figure 5:
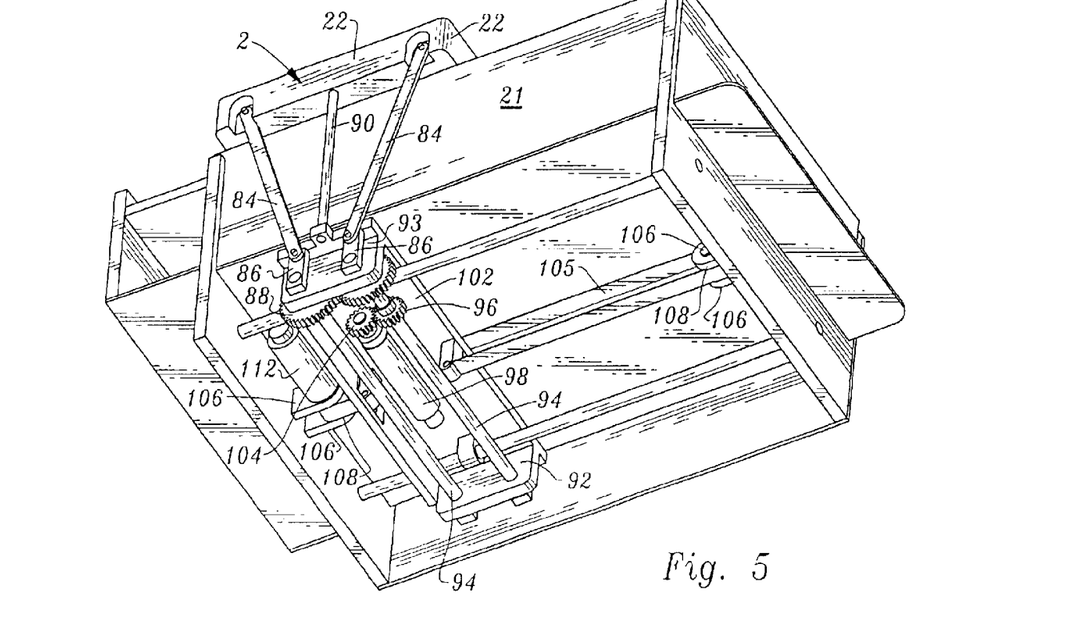
FIG. 5 is a lower perspective view of that which is shown in FIG. 4.

The housing 20 overlies a substantially box-shaped interior 21 (FIGS. 5 and 10) having the first and second chambers 4, 6 disposed in substantially side by side relationship, interrupted one from the other by a dividing wall 8. Each chamber is a substantially box-shaped hollow enclosed by three sidewalls 12 and the common dividing wall 8 and includes a floor 14. A top surface of the housing interior 21 includes a relief area 16 circumscribing each of the chambers, the relief area 16 dimensioned to receive a gasket 18 carried on the lower periphery of carriage frame 2. The carriage frame 2 is substantially a rectangular construct having four sides 22 leaving an open top and an open bottom. The open top includes a peripheral chamfer 24 to insure tight nesting of the sample plate 40 and a seal which will support a vacuum.

Figure 3:
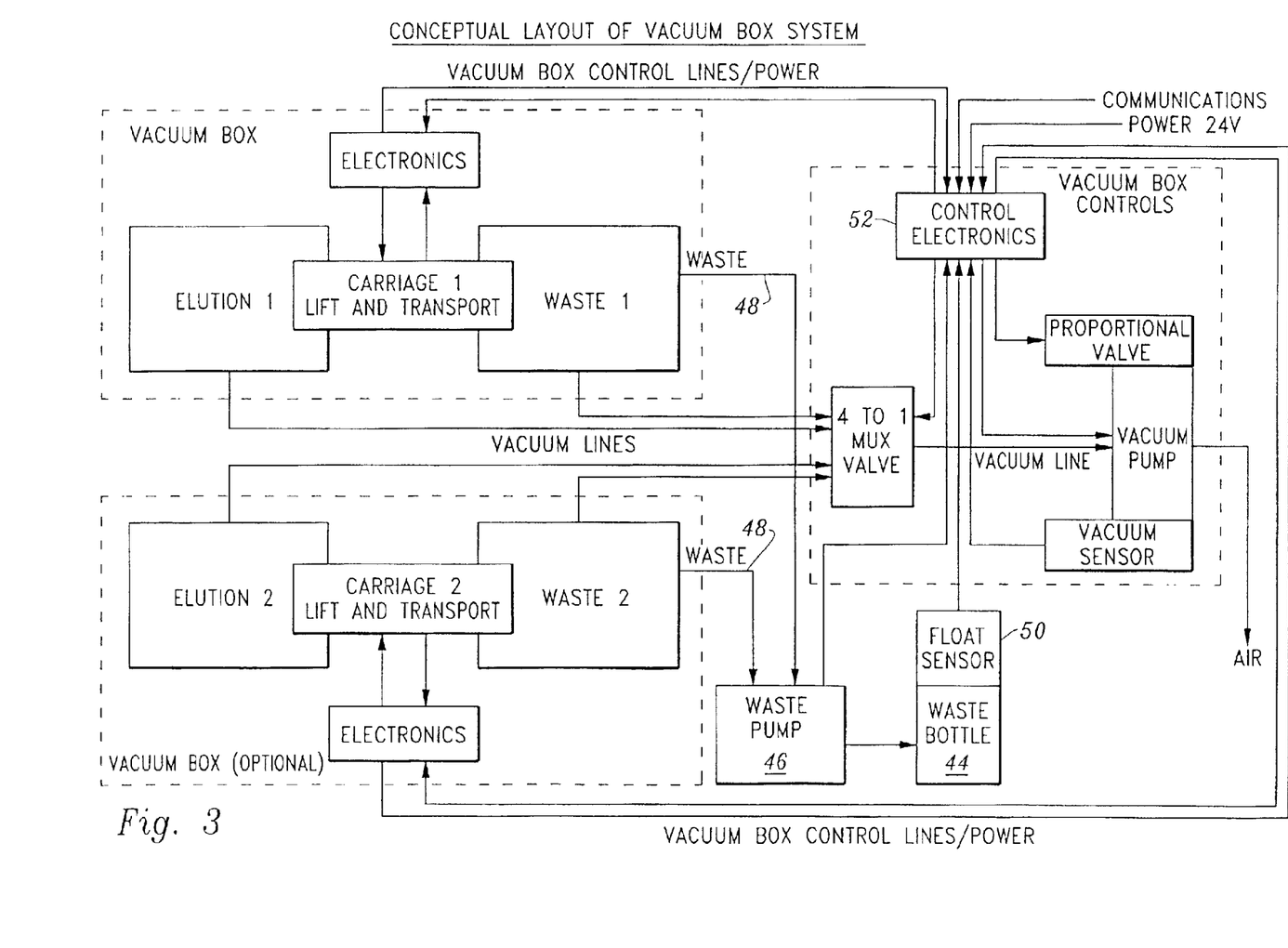
FIG. 3 is a conceptual flow chart of two vacuum box layouts, plumbed to a common vacuum pump, waste disposal and control system.

The first chamber 4 is regulated to waste as from system washing or purging and includes a drain line 26 passing through its bottom wall 14. An opening 28 extends through a sidewall 12 from which to draw a vacuum. In addition, the first (waste) chamber 4 receives both a waste container 30 resting on its floor 14 and an isolation plate 32 resting on the waste container 30. The waste container 30 is essentially an opened top box having a bottom wall 34 and peripheral sidewalls 36 in which the bottom wall 34 includes an opening 38 which communicates with a drain opening in the first chamber 4 and mates therewith by means of a drain stem 42 extending between the drain line 26 and opening 38 to allow waste material to be collected in the waste container 30 and subsequently pumped therefrom into a waste bottle 44 (FIG. 3) via pump 46. As shown in FIG. 3, the drain line 26 communicates via a conduit 48 to the waste pump 46 which transfers waste from the waste container 30 to a waste bottle 44 which is provided with an integrated float and sensor 50 so that when the waste bottle 44 nears being filled, the sensor coupled to the float communicates with control electronics 52 to provide a signal on the screen of the computer 110 to denote that it is time to empty or replace the waste bottle 44.

Figure 12:
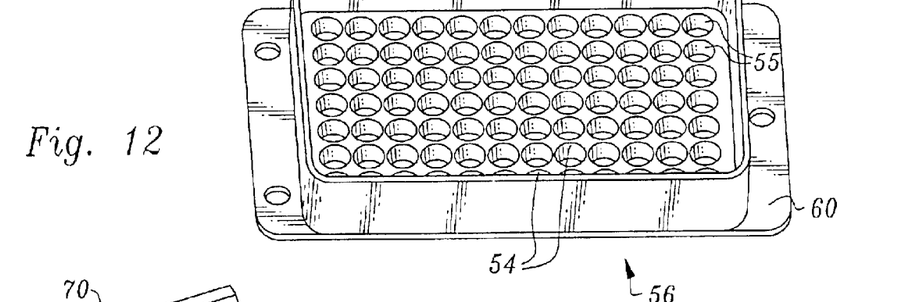
FIG. 12 is a perspective view of waste side isolation plate shown in FIGS. 9 and 10.

FIG. 12 reflects details of the bottom surface 56 of the waste isolation plate 32 which in effect provides isolation of each open end of the sample plate 40 when the open ends 72 penetrate within wells 54 of the isolation plate for their washing. As shown in FIG. 12, the isolation plate 32 includes a downwardly extending peripheral skirt 58 dimensioned to depend within the waste container 30 upon a shelf 60 formed on a top surface of plate 32. The number of wells 54 and their dimension are calculated to each receive one open end of the sample plate 40. The wells have sidewalls 55. By having the lowermost portion of each open end isolated within one well on the isolation plate, the fluid in the sample plate can be vacuum-pulled downward with minimal concern of "cross-talk" (i.e., splatter) between each open end 72 which could otherwise introduce error during subsequent operations.

Figure 10:
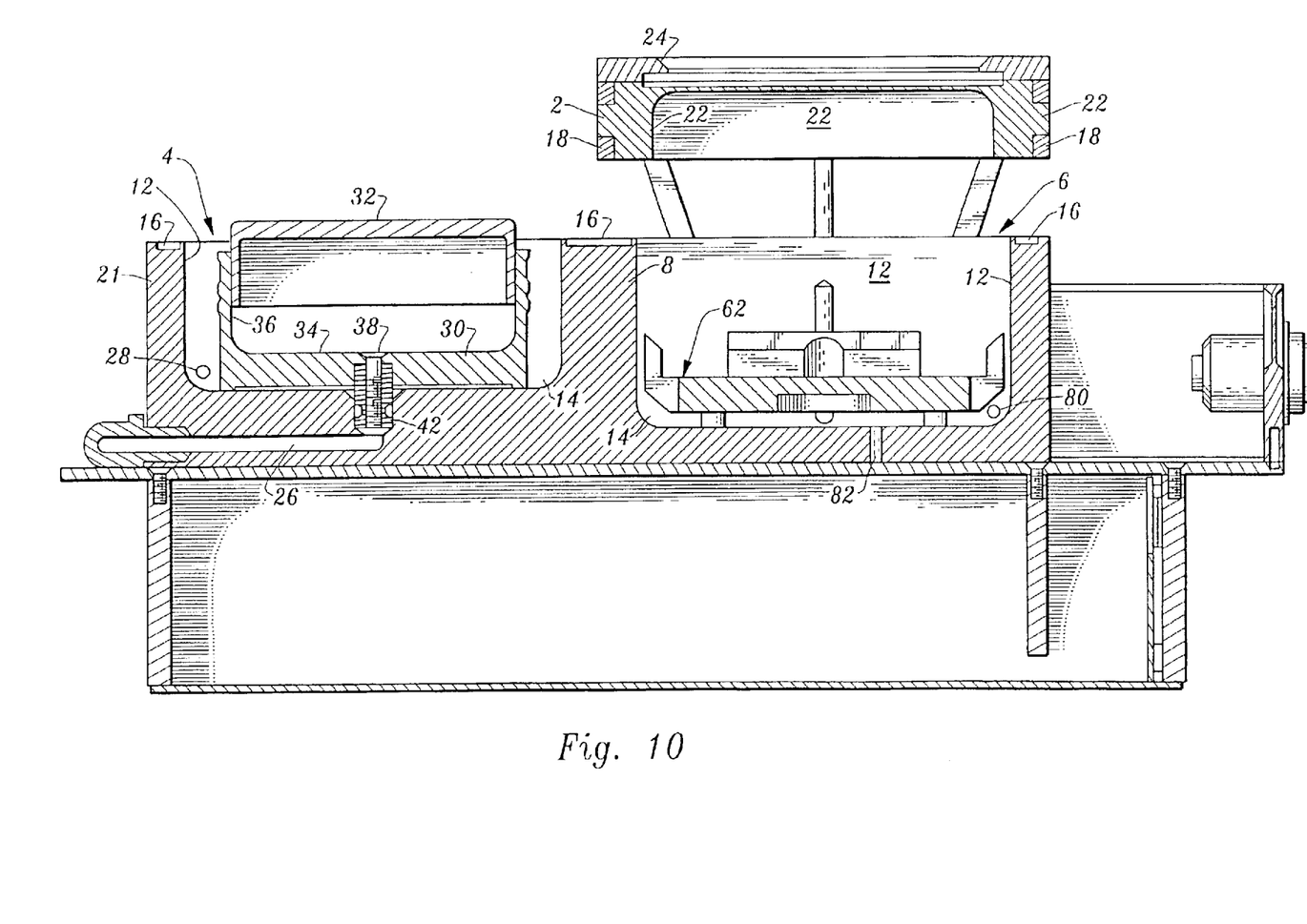
FIG. 10 is a sectional view of the shuttle mechanism taken along lines 10—10 of FIG. 9.
Figure 11:
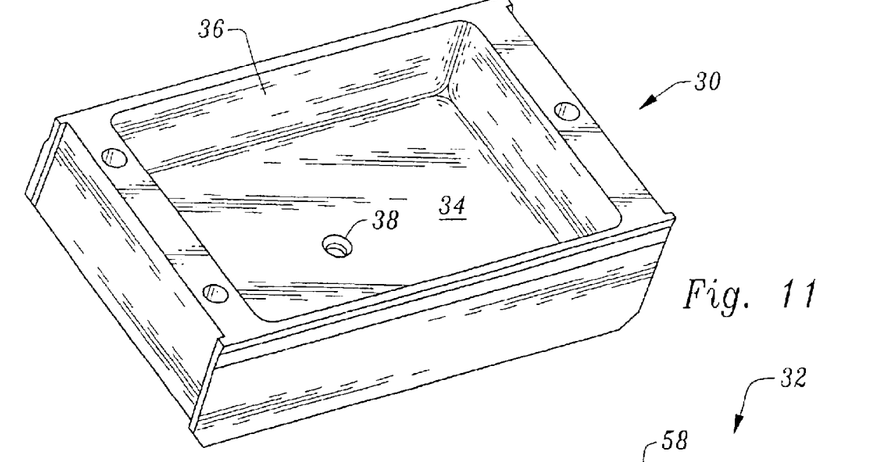
FIG. 11 is a perspective view of the waste container shown in FIG. 10.
Figure 13:
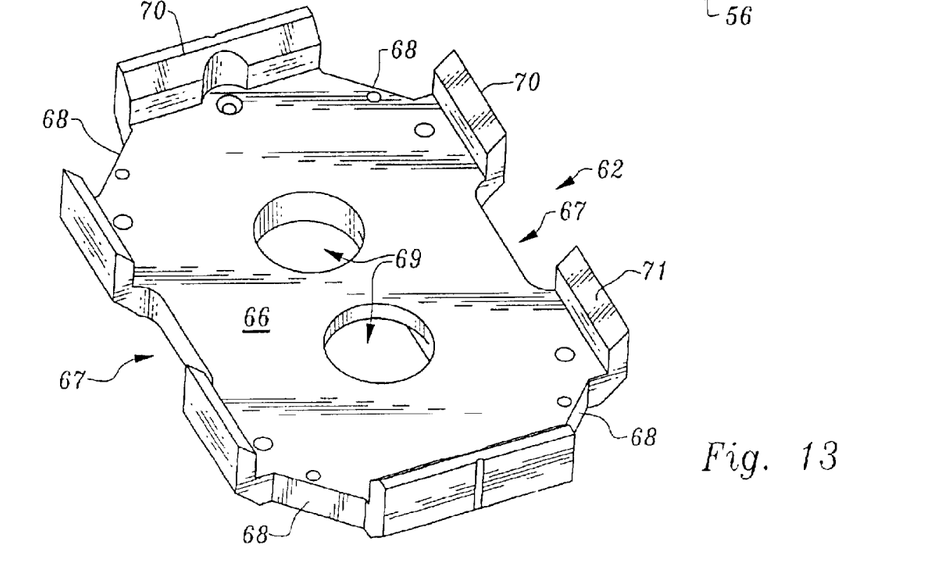
FIG. 13 is a perspective view of the elution side collection plate positioner shown in FIGS. 9 and 10.

The second (elution) chamber 6 is a similarly dimensioned well having a floor 14 and peripheral walls 12 (FIG. 10). A positioner 62 is located on the floor 14 of the second chamber 6 and maintains a collection plate 64 (FIG. 4) in a fixed position. As shown in FIGS. 10 and 13, the collection plate positioner 62 includes a base 66 of substantially rectangular planar configuration having truncated corners 68 such that these corners are mitered at a substantially forty-five degree angle. Adjacent each of these mitered corners are vertically upstanding marginal portions 70 which project above the base 66 and are fashioned to somewhat parallel the interior sidewalls 12 of the second chamber 6. These marginal portions 70 are on all four sides of the base 66 and include latitudinal and longitudinal margins. The longitudinal margins have interruptions 67 medially disposed. Two holes 69 pass through the base 66, equispaced from a transversely disposed centerline with respect to the longitude of the collection plate positioner 62. In one form of the invention, the marginal portions 70 have inwardly chamfered top surfaces 71 sloping down from the peripheral sidewalls 8, 12 of the second chamber. These marginal portions 70 subsequently accurately position the collection plate 64 since its orientation within the elution chamber 6 is important to assure vertical registry when the sample plate 40 is held in overlying relationship. It is important to note that the sample plate 40 typically includes downwardly projecting open ends 72 (FIG. 4) corresponding in number to each of the probe tips 155 associated with the probe assembly 150. Thus, it is important that each open end 72 on the sample plate 40 have a corresponding well opening 74 within the collection plate 64 in vertical alignment therewith to assure a minimal cross-talk between adjacent specimens represented by tips 155 and open end 72. One feature of the instant invention is that various collection plate positioners 62 may have different vertical dimensions (as by the height of marginal portions 70) so that the positioner 62 can control the distance that exists between the collection plate 64 and the sample plate 40. It is desired that this relationship between the collection plate 64 and the sample plate 40 be held within close tolerances so that the lowermost extremity of each open end 72 of the sample plate 40 resides at least partially within a corresponding well opening 74 of the collection plate 64 to guarantee accurate deployment of the fluid therewithin without migration to an adjacent well opening. A site window 78 (FIG. 4) is provided passing through the lid 22 so that upon assembly, the proper relationship between the collection plate 64 and the sample plate 40 can be assured. The second chamber 6 is similarly provided with a vacuum portal 80 (FIG. 10) to draw fluid down from the sample plate 40 into the collection plate 64, similar to the first chamber 4. The second chamber 6 preferably does not, but may also include a drain 82 similar to the first chamber 4.

As mentioned, the carriage frame defines one component of a lift and transport carriage assembly which allows the carriage frame to move between the first and second chambers.

Specifically, and with reference to FIGS. 5 through 10, the carriage frame 2 is shown as including at least one gasket 18 along its bottom peripheral edge. The carriage frame is defined by a circumscribing wall 22 of substantially rectangular shape open at its bottom and top and provided with a chamfer 24 around its top inner periphery so that the sample plate 40 can nest securely therewithin.

Figure 6:
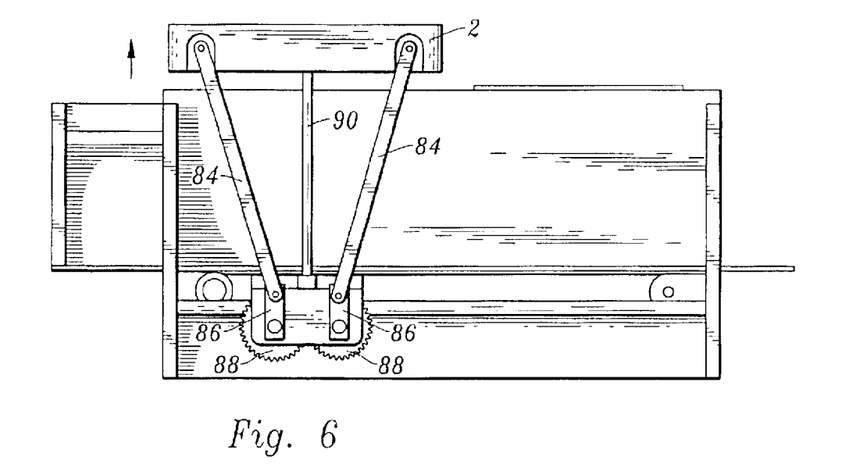
FIG. 6 is a side view of the FIG. 4 shuttle mechanism in a first motion.
Figure 7:
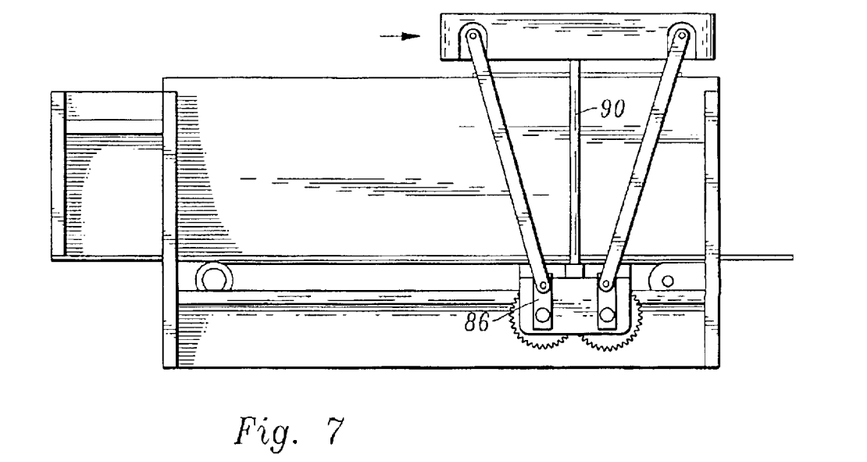
FIG. 7 is a side view of the shuttle mechanism in a second motion.
Figure 8:
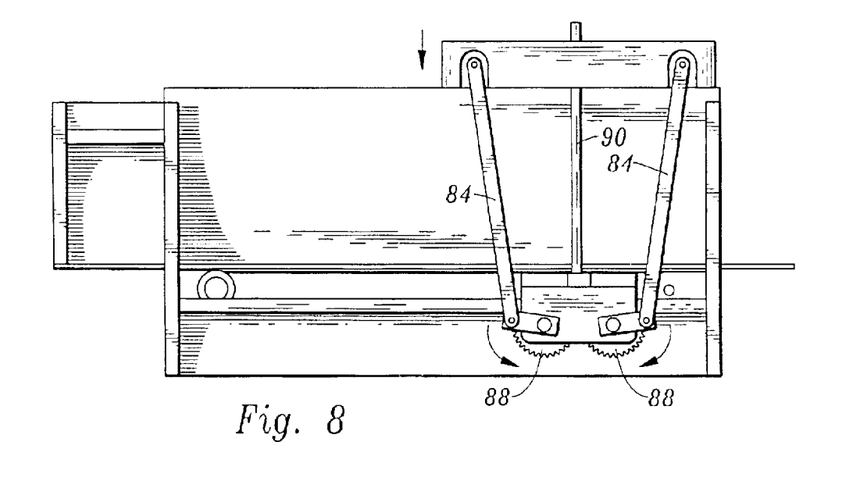
FIG. 8 is a side view of the shuttle mechanism in a third motion.
Figure 9:
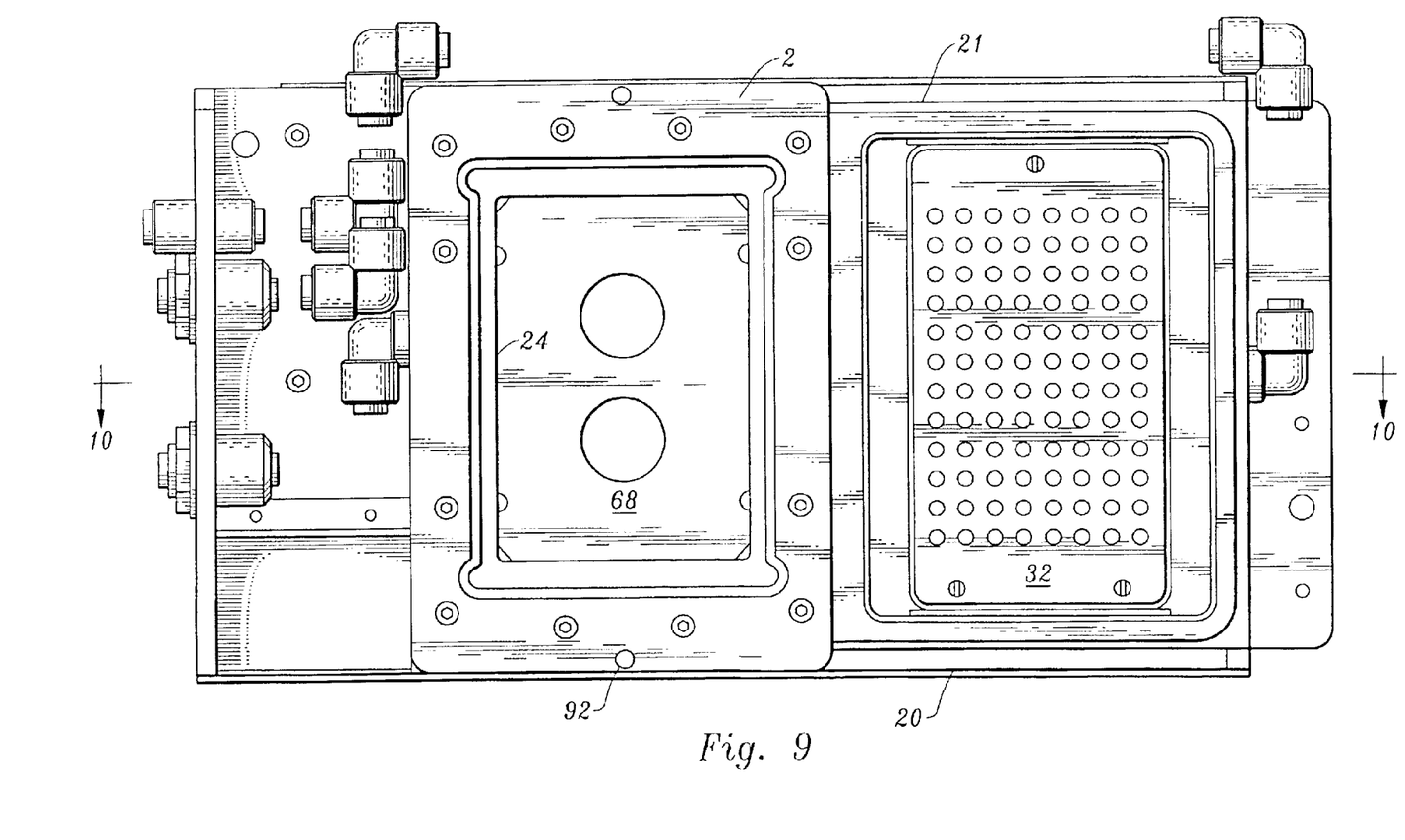
FIG. 9 is a top plan view of the shuttle mechanism.

The carriage frame 2 has, on two opposed sides thereof, first and second lift rods 84 that are pivoted adjacent corners of the frame 2. Each of the four lift rods 84 has a remote end which terminate in a cam link 86 at each end thereof. The cam links 86 in turn are connected to gear pairs 88 which are held in meshing engagement. Thus, when the gears rotate as shown in FIG. 8, the carriage frame moves from the upward position shown in FIG. 6 downwardly to the position shown in FIG. 8. Conversely, when the gears shown in FIG. 8 rotate in a direction opposite from the arrows as shown thereat, the carriage frame moves upwardly as shown in FIG. 6. The carriage frame is held stable by means of two slide rods 90, medially disposed between the lift rods 84 and on the sides of the carriage frame that receive the lift rods 84. Two bores 92 (FIG. 4) pass through the carriage frame 2 to receive the slide rods 90 so that when the carriage frame is in its lowermost position (FIG. 8), a free end of the slide rod 90 projects upwardly from the carriage frame (FIG. 8). Each slide rod 90 is attached at its opposite end to a support plate 93 (FIG. 5) through which gears' shafts 94 project and fix to the cam links 86. The support plates 93 depend from a trolley 102 at extremities thereof. These gear shafts 94 (FIG. 5) extend between the support plates 93 and drive the gear pair 88 to move the transport carriage assembly. One of the gear shafts includes a driven gear 96 which is driven by a drive motor 98 depended from an underside of the trolley 102, intermediate the support plates 93. As the drive motor 98 rotates, its drive gear 104 rotates the driven gear 96 on one of the two shafts 94 as shown, which in turn drives the gear pair 88 to effect motion of the lift rods 84 as described.

In addition, the lift and transport carriage assembly includes a drive belt 105 spanning the length of the vacuum box and transverse to the long axis of the drive gear shafts 94. The drive belt 105 is held in position at remote extremities by means of pulley tabs 106, pairs of which each have an interposed pulley 108 therebetween. The drive belt 105 is looped over each pulley 108 and a portion of the drive belt is operatively coupled to the trolley 102. When the drive belt 105 is driven by means of a belt motor 112 shown in FIG. 5, the trolley can move from over the first chamber 4 to the second chamber 6 and back as suggested by the horizontal arrow in FIG. 7. Note that it is preferred that the carriage frame 2 be in the uppermost FIG. 6 position prior to linear translation. The drive motor 112 for the belt 105 is fixed on an underside of the vacuum box and operatively coupled to the belt 105 or one pulley 108.

The computer 110 is operatively coupled to control the robotic arm 200 in grasping, inter alia, sample plates 40 and operating the vacuum pump and waste pump as well as powering the transport mechanism and the pipette operation.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A sample treatment device, comprising, in combination:
- a housing having plural chambers, one of said chambers including means for directing waste fluid from said chamber to a waste storage area, said waste storage area operatively coupled to said one said chamber by means of a pump;
- a sample plate;
- means to expose said sample plate to one chamber in said housing;
- extraction means operating on the sample plate addressing the sample plate to the one chamber, said sample plate in fluid communication with said one chamber, whereby said extraction means extract components of interest from samples residing in said sample plate; and
- shuttle means to selectively present the sample plate to one of the plural chambers for the throughpassage of fluid from the sample plate, said shuttle means including:
  - a carriage frame upon which said sample plate is placed,
  - lifting means for elevating said carriage frame from a first elevation to a second elevation, and
  - means for translating said carriage frame laterally along a substantially horizontal plane, wherein said lateral translation means includes a belt driven trolley which moves in response to motion of said belt.

2. The device of claim 1 wherein said means to expose said sample plate to one chamber in said housing includes an open top and bottom of said carriage frame, said carriage frame formed from a rectangular construct having four sides.

3. The device of claim 2 wherein said lifting means includes two pairs of lift rods extending between said carriage frame and two pairs of cam links, said cam links connected to a pair of shafts, two links per said shaft and said cam links driven by a pair of meshing gears, one said gear mounted per shaft, and one said shaft driven by a motor.

4. A sample treatment device, comprising, in combination:
- a housing having plural chambers, one of said plural chambers including a positioner located on a floor of one said chamber, said positioner including a marginal portion which projects upwardly from said positioner to support a collection plate thereupon;
- a sample plate;
- means to expose said sample plate to one chamber in said housing;
- extraction means operating on the sample plate addressing the sample plate to the one chamber, said sample plate in fluid communication with said one chamber, whereby said extraction means extract components of interest from samples residing in said sample plate; and
- shuttle means to selectively present the sample plate to one of the plural chambers for the throughpassage of fluid from the sample plate.

5. A sample treatment device, comprising, in combination:
- a housing having plural chambers, one of said plural chambers including a waste container resting on a floor of said one chamber having an isolation plate resting on said waste container, said waste container and said one chamber provided with means for removing waste fluid therefrom;
- a sample plate;
- means to expose said sample plate to one chamber in said housing;
- extraction means operating on the sample plate addressing the sample plate to the one chamber, said sample plate in fluid communication with said one chamber, whereby said extraction means extract components of interest from samples residing in said sample plate; and
- shuttle means to selectively present the sample plate to one of the plural chambers for the throughpassage of fluid from the sample plate.

6. The device of claim 5 wherein said sample plate has open ends and said isolation plate includes a downwardly extending peripheral skirt dimensioned to depend within said waste container from a shelf located on said isolation plate, and said isolation plate includes a plurality of wells passing through said isolation plate having a dimension such that when said open ends on said sample plate project within said wells, each said open end is protected from cross-talk with adjacent said open ends.

* * * * *